United States Patent [19]

Hodgson et al.

[11] Patent Number: 5,095,740
[45] Date of Patent: Mar. 17, 1992

[54] SYSTEM FOR MONITORING AND ANALYZING SOLID CONTAMINENTS IN FLUIDS

[75] Inventors: Kim A. Hodgson; James C. Fitch, both of Tulsa, Okla.

[73] Assignee: Diagnetics, Inc., Tulsa, Okla.

[21] Appl. No.: 714,336

[22] Filed: Jun. 12, 1991

Related U.S. Application Data

[63] Continuation of Ser. No. 143,242, Dec. 31, 1987, abandoned, which is a continuation of Ser. No. 765,795, Aug. 15, 1985, abandoned.

[51] Int. Cl.⁵ .............................................. G01N 15/00
[52] U.S. Cl. ........................................ 73/61 R; 210/340
[58] Field of Search ............... 73/61 R; 210/340, 341

[56] References Cited

U.S. PATENT DOCUMENTS

| | | | |
|---|---|---|---|
| 3,010,583 | 11/1961 | Kenyon | 73/863.23 |
| 3,266,299 | 8/1966 | Swank | 73/61 R |
| 3,452,586 | 7/1968 | Childs et al. | 73/61 R |
| 3,455,146 | 7/1969 | Smith et al. | 73/61.4 |
| 3,499,315 | 3/1970 | Marino | 73/61 R |
| 3,686,926 | 8/1972 | Miller et al. | 73/61 R |
| 3,746,167 | 7/1973 | Arthur | 73/61 R |
| 3,872,710 | 3/1975 | Louvel | 73/61.4 |
| 3,900,290 | 8/1975 | Hornstra | 73/61 R |
| 3,976,572 | 8/1976 | Reick | 73/61 R |
| 3,997,297 | 12/1976 | Jenkins et al. | 422/93 |
| 4,181,009 | 1/1980 | Williamson | 73/61.4 |
| 4,389,879 | 1/1983 | Bach et al. | 73/61 R |
| 4,446,728 | 5/1984 | Hockenberry | 73/61.4 |
| 4,495,799 | 1/1985 | Fisher et al. | 73/61 R |
| 4,583,396 | 4/1986 | Hunt et al. | 73/61 R |
| 4,786,473 | 11/1988 | Mukogawa et al. | 73/61 R |
| 4,973,406 | 11/1990 | Ponzielli | 210/340 |

FOREIGN PATENT DOCUMENTS

WO84816 3/1984 PCT Int'l Appl. .

*Primary Examiner*—Hezron E. Williams
*Assistant Examiner*—Shu-Cheng Kau
*Attorney, Agent, or Firm*—Head and Johnson

[57] ABSTRACT

A system for determining the level of particulate contaminants in a fluid utilizes a porous filtration element having filtration pores therethrough in fluid series with a volume indicator. Preferably, the filtration medium is provided with filtration pores which have a generally predetermined size such that oversized particles of the particulate contaminants are accumulated on one side of the filter medium. In one embodiment, filtration of the fluid continues until the filtration medium is blocked entirely, and then a reading of the volume of fluid which has flowed therethrough is taken. The fluid thus accumulated can be forced back through the filter medium in a backflush direction such that the accumulated particulate contaminants are washed away, thereby rendering the filtration medium ready for a subsequent measurement. In automatic embodiments of the invention, a bistable valve may be utilized, the flow states of the valve being switched to shift from the filtration phase to the backflush phase. A pressure comparison arrangement obviates the need for clogging the filtration medium completely during each measurement phase. This is achieved by issuing a signal when the flow through the filtration medium is reduced to a predetermined level.

23 Claims, 5 Drawing Sheets

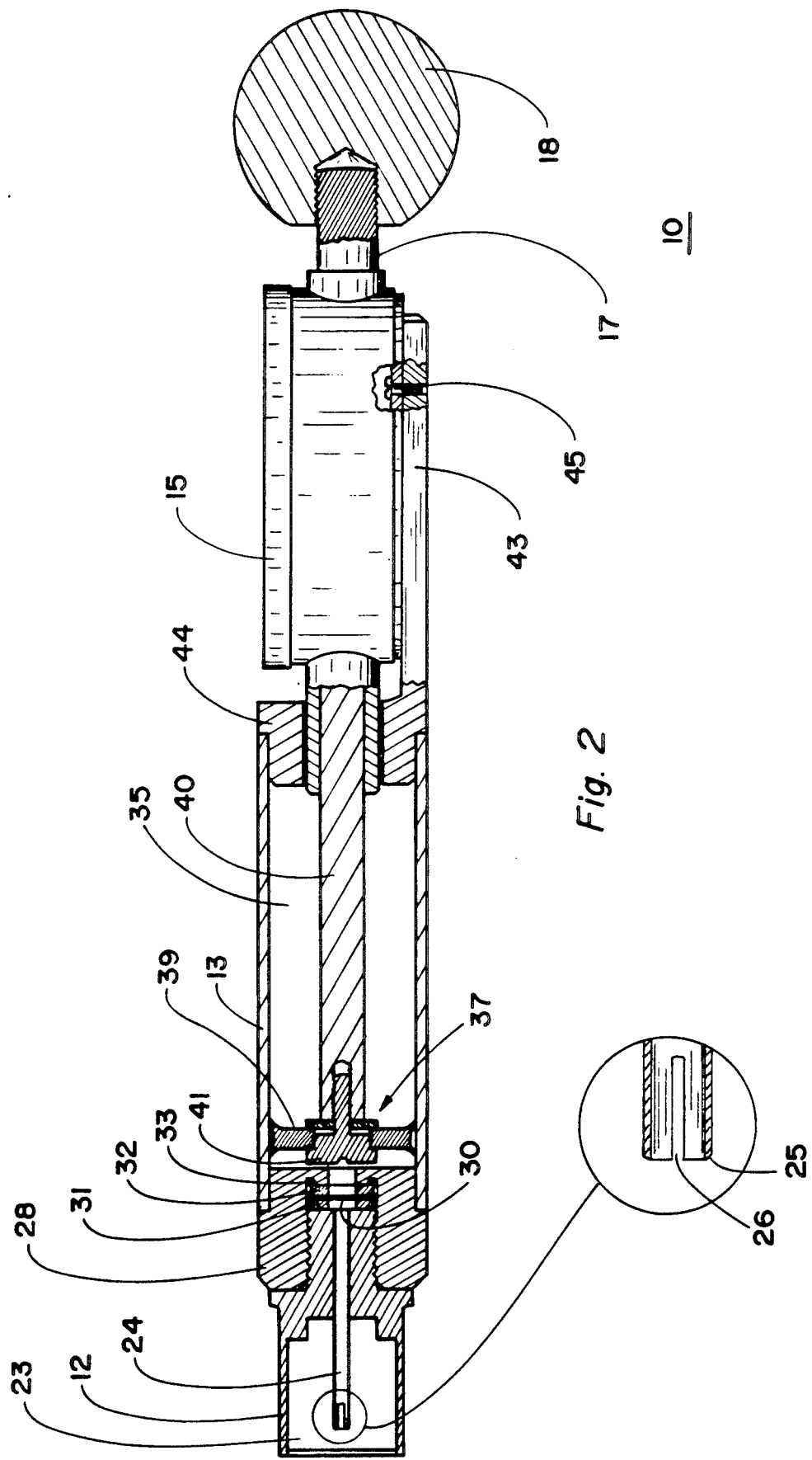

SYSTEM FOR MONITORING AND ANALYZING SOLID CONTAMINENTS IN FLUIDS

This is a continuation of copending application Ser. No. 07/143,242 filed on Dec. 31, 1987, now abandoned, which is a continuation of application Ser. No. 06/765,795 filed Aug. 15, 1985, now abandoned.

BACKGROUND OF THE INVENTION

This invention relates generally to arrangements and methods for determining the level of particulate contaminants in fluids in a fluid system, and more particularly, to a system whereby the fluid is passed through a filter medium having a substantially predetermined pore size; the contamination level being determined by measuring the volume of fluid passing through the filter medium prior to the blockage thereof causing a reduction of fluid flow therethrough to a predetermined level.

In fluid systems, particularly tribological systems such as hydraulic, lubricating, fuel, and many process systems, it is essential to detect and measure the concentration of particulate contaminants entrained in the fluids. It is well known that high levels of such contamination will dramatically decrease the efficiency and life of machinery associated with such fluids.

The most common technique for measuring the contamination levels of fluids requires microscopic or photoelectric counting. The systems required for performing such counting are generally not portable or too delicate for field use, thereby requiring a laboratory environment for their use. Some of the currently known methods which are used to quantify the concentration of particles in a fluid employ gravimetric and volumetric techniques, so as to assess the silting effects of particulate contamination in the fluids. ASTM F52-65T cites an apparatus which is useful in obtaining the silting index.

A further known approach to obtaining of a measure of the contamination of a fluid utilizes a photoelectric system which generates a form of light which is passed through the fluid and detected by a photodetector. The level of contamination of the fluid is inversely related to the intensity of the light which reaches the photodetector. It is a problem with such light-dependent contamination sensors that they are too delicate for installation directly on machines which are subject to vibration and shock, and which are exposed to hostile environmental conditions. Additionally, the calibration of such sensors for each type of fluid and for the various types of entrained contaminants requires extensive on-site or on-board instrumentation which substantially increases the cost of such a system beyond what can be justified for the fluid systems.

The silting index method of determining the degree of contamination is essentially a laboratory-oriented technique which provides a semiquantitative assessment of particulate contamination in the silt size range of between approximately 0.5 to 5.0 micrometers. In essence, this known method measures the decay in the rate of fluid flow resulting from the clogging of a membrane when a contaminated fluid sample is passed therethrough. Particles having a size greater than the pore size of the membrane are retained by the filter medium membrane. It is a problem with the method that it is characterized by poor repeatability because particles which are much greater in size than the silt sized pores of the membrane form a loose, open filter cake, while particles having a smaller size than the pore size, or stable gels resulting from oxidation products and polymers, tend to block the pores of the membrane in an unpredictable manner.

A further known system for determining the level of contamination in a fluid utilizes the passing of the system fluid through a filter medium until a predetermined pressure drop is achieved across the filter medium. The level of contamination in the fluid is determined by measuring the time required to reach the predetermined pressure level. This method, therefore, has several problems. First, the known method is sensitive to the pressure level of the system upstream of the sensing filter medium, thereby requiring the use of an auxiliary pump to circulate a stream of the fluid at a constant pressure. This known system, therefore, produces a contamination indication which is subject to the effects of system flow rate, system pressure differential, and fluid viscosity. Correction of the results produced by this system to compensate for such effects would require substantial additional cost.

It is, therefore, an object of this invention to provide a fluid contamination monitoring system which is simple and inexpensive.

It is another object of this invention to provide a fluid contamination measurement system which is easily portable and rugged enough for field use.

It is also an object of this invention to provide a contamination level analyzer and monitor system which can be integrated as part of a fluid system.

It is additionally an object of this invention to provide a fluid contamination level analyzer and monitor system which can provide continuous evaluation of the fluid.

It is also an object of this invention to provide a fluid contamination analyzer and monitor which is resistant to the adverse effects of the contaminant in the fluid.

It is another object of this invention to provide a contamination level monitoring device which is insensitive to fluctuations in the rate of fluid flow.

It is a still further object of this invention to provide a system for measuring the contamination level of a fluid and which is insensitive to fluctuations in the fluid pressure.

It is still another object of this invention to provide a system for determining the level of contamination in a fluid which is insensitive to temperature variations of the fluid and the ambiance.

It is yet another object of this invention to provide a fluid contamination measuring system which is insensitive to the viscosity of the fluid.

Another object of this invention is to provide a contamination monitoring system which discriminates between particles of different sizes.

A further object of this invention is to provide a contamination monitoring system which is responsive to the concentration of particles in a designated size range.

Another object of this invention is to provide repeatable and reliable fluid contamination measurements throughout a wide range of contamination levels.

A still further object of this invention is to provide a contamination measuring system which exposes the detection element to the fluid flowing within the system.

A yet further object of this invention is to provide a contamination measuring and analyzing system which utilizes a filter medium which can be rejuvenated by backflushing.

Still another object of this invention is to provide a contamination measuring system which samples the fluid in a fluid system automatically.

A yet further object of this invention is to provide a system for detecting the level of contamination of a fluid with respect to a predetermined range of particle sizes.

Still another object of this invention is to provide a particulate contamination monitoring system which can be simply and inexpensively adapted to various size ranges of particulate contaminants.

SUMMARY OF THE INVENTION

The foregoing and other objects are achieved by this invention which provides a contamination measurement arrangement for determining the level of particulate contamination in a fluid. In accordance with the invention, a porous filtration medium having filtration pores therethrough for passing the fluid is provided. The filtration pores are sized within a predetermined range of filtration pore dimensions such that oversized particles of the particulate contaminants in the fluid which have particle dimensions greater than the sizes of the filtration pores are prevented from passing therethrough. A volume indicator is arranged, illustratively in tandem with the porous filter, to provide an indication corresponding to the volume of the fluid which has passed through the filtration pores.

In one highly advantageous embodiment of the invention, a backflush arrangement is provided for urging a fluid through the filtration pores in a second direction of fluid flow. This reverse flowing fluid may be the fluid which was stored in the volume indicator, and serves to flush away the oversized particles of the contamination which have accumulated on the porous filter.

In one embodiment, the backflush arrangement cooperates with the volume indicator and shares certain of the components. For example, fluid which flows through the porous filter is accumulated in a chamber having a piston slidably arranged therein. As the volume of the fluid is increased, the piston is displaced along the chamber so as to produce an increasing volume which accommodates the fluid. The displacement of the piston is monitored and serves to indicate the accumulated volume of the fluid. In the operation of one embodiment of the invention, fluid is continued to be filtered through the porous filter until the flow is terminated by blockage resulting from the accumulation of particulate contaminants at the porous filter. The overall displacement of the piston is then measured, as indicated herein, to provide an indication of the level of particulate contaminants for the indicated volume of fluid.

In a manual and portable embodiment, the piston is coupled to a manual actuator which can be manipulated by an operator to drive the piston in a direction opposite to the original displacement. Thus, the fluid stored in the expandable chamber is forced back through the porous filter in the reverse direction so as to clear the blockage and prepare the apparatus for a subsequent measurement.

In an automatic embodiment of the invention, a hydraulic actuator is arranged to urge the piston in the backflush direction in response to a high fluid pressure. In such an embodiment, the fluid at elevated pressure is available from a pressurized portion of the fluid system.

Preferably, the application of such an elevated pressure in the reverse flow direction is achieved by a selectable fluid coupling arrangement, which may include a solenoid-operated valve. When the valve is in a first flow state, the fluid from the pressurized portion of the fluid system is conducted through the porous filter and stored in the expandable chamber. In a second state, the valve directs the fluid from the pressurized portion of the fluid system in the backflush direction. A control system may be provided to record the measurements of the displacement of the piston, and initiate the backflush operation when fluid flow through the porous filter has ceased. In certain embodiments of the invention where relatively high fluid pressures are available from the fluid system, a safety relief valve is employed to limit the fluid pressure applied across the porous filter. The connection of the relief valve to the porous filter may be achieved through an arrangement of check valves. In a preferred embodiment, the relief valve is of the direct acting type so as to maintain a relatively constant differential pressure across itself.

Very high rates of fluid flow are undesirable as they produce excessive pressure drops across various valves of the system and associated fluid passageways. It is desirable that such pressure drops remain small in comparison with the pressure setting of the relief valve. The fluid flow is limited by the interposition of a restricting orifice which is arranged in the fluid path of the porous filter.

It may be desirable in certain embodiments not to effect a complete blockage of the porous filter before a reading of the level of contamination can be taken. In such an embodiment, the level of contamination may be determined in response to the volume of the fluid which is collected before the magnitude of the fluid flow through the porous filter is reduced to a predetermined level greater than zero flow. Such a nonzero fluid flow can be determined by monitoring the pressures across the restricting orifice and the porous filter or to measure the rate of volume of fluid passing through the screen per unit time. When the rate of volume reaches a valve then total volume is measured. Thus, when the pressure drop across the porous filter exceeds a predetermined percentage of the pressure drop across the restricting orifice, an indication may be provided which would indicate the termination of the measurement phase. At such time, the volume of the fluid which has passed through the porous filter may be measured, and a backflush procedure initiated to prepare the system for a subsequent measurement.

In accordance with one embodiment of the invention, the pressure differentials across the porous filter and the restricting orifice are compared against one another in a pressure differential monitoring arrangement which utilizes a stator and a slidable piston therein. The piston is arranged to present a plurality of surfaces having effective surface areas to respective ones of the pressure signals. In one specific illustrative embodiment of the invention, the surfaces are arranged with respect to one another to have a proportion ratio of $1:K:(K+1)$. With this arrangement, the multifaced piston arrangement is displaced to one side when the pressure across the porous filter exceeds $1/K \times 100\%$ of the pressure across the restricting orifice. Any of several known indicator arrangements, such as a limit switch or a proximity switch, may be used to provide an indication corresponding to the displacement of the piston.

A further porous filter having filtration pore dimensions different from those of the original porous filter, and an associated further volume measurement arrangement, may be provided to facilitate measurement of particulate contaminants in two particle size ranges simultaneously. In an embodiment where the porous filter is formed of a detection mesh, the pore size can be tailored to meet the size discrimination requirements of the particular application. Thus, one or both such porous filters can be responsive to particle sizes greater than any give size, illustratively 5, 10, 12, 20 or other micrometer sized particles. The use of dual units can be effective to measure the contaminant size range, in accordance with current standards such as ISO 4406.

The porous filter medium may be formed of any of several known materials in the form of a filter screen. Such a filter screen may be formed as a wire screen, an electroformed metal screen, a sintered metal, or a synthetic thermoplastic consisting of a thermal set plastic arranged as a woven monofilament fabric. A resilient seal is provided to prevent flow of the fluid around the filter screen, and may consist one or more polypropylene gaskets which are bonded, or ultrasonically welded, to the filter medium.

In accordance with a method aspect of the invention, the level of particulate contaminants in the fluid of a fluid system is measured by passing a portion of the fluid in a first flow direction through a filter medium of predetermined pore size, and measuring the volume which is passed through the filter medium before the rate of flow of the fluid is reduced to a predetermined rate of flow. In certain embodiments, the predetermined rate of flow of the fluid may be substantially zero, corresponding to essentially complete blockage of the filter medium by the particulate contaminants. In other embodiments, however, the fluid flow may be reduced to a level greater than zero, and therefore corresponding to less than complete blockage of the filter medium.

A backflushing procedure is applied to the porous filter such that the accumulated contamination is washed away. In some embodiments of the invention, particularly in automatic contamination measurement systems, such backflushing can be achieved by reversing high and low pressure portions of the fluid system with respect to the filter medium. Such reversal may be achieved by the solenoid-operated valve described hereinabove.

In those embodiments of the invention where a measurement of the contamination level is taken before the porous filter is blocked completely, the present method invention includes the step of monitoring the pressure differential across the filter medium and the restriction orifice, respectively. The volume can be determined by measuring the displacement of a hydraulic piston, by an integrating flow meter, or by use of a graduated cylinder or measuring cup. The volume of fluid is then related in terms of the particle count of the accumulated particulate contaminants, or the gravimetric level for a known particle distribution, or some other acceptable expression of contamination level.

BRIEF DESCRIPTION OF THE DRAWINGS

Comprehension of the invention is facilitated by reading the following detailed description in conjunction with the annexed drawing, in which:

FIG. 2 is a partially cross-sectional side view of the embodiment of FIG. 1;

DETAIL DESCRIPTION

Figure 1:
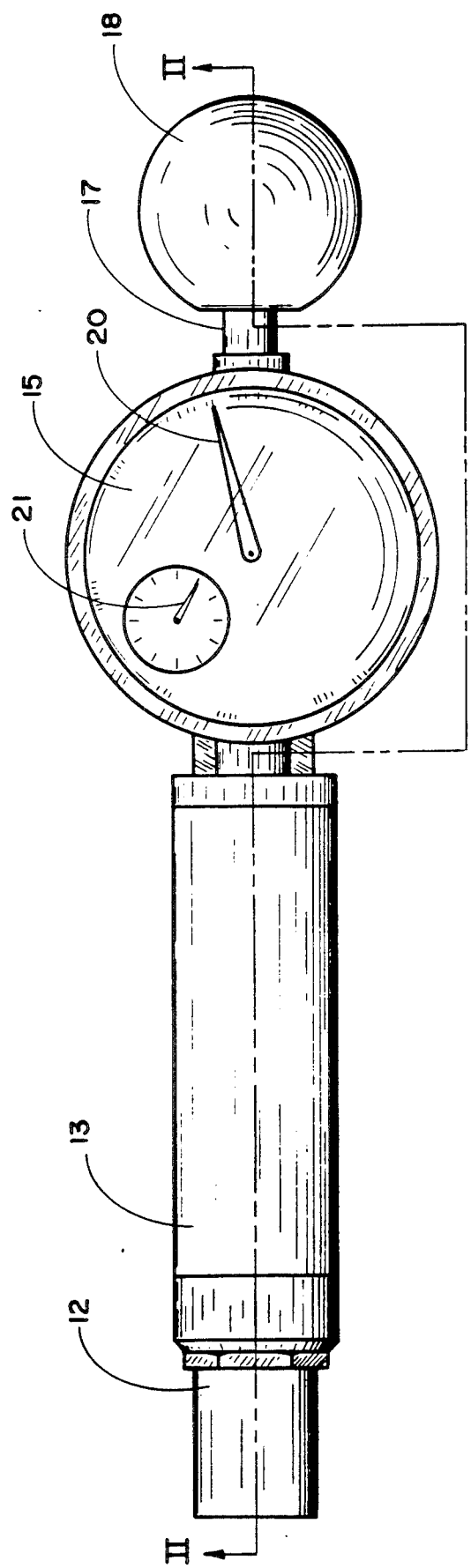
FIG. 1 is a plan view of a manually operable portable embodiment of the invention.

FIG. 1 shows a portable, manually operable embodiment of a fluid contamination measurement arrangement 10. As shown in this figure, arrangement 10 has a coupling portion 12, connected to a variable volume chamber 13. Arrangement 10 is further provided with a dial indicator 15 which is arranged to provide an indication of the volume of variable volume chamber 13. On the other end of dial indicator 15 from the variable volume chamber is arranged a rod 17 with a handle ball 18 affixed thereto. Although handle ball 18 has a somewhat spherical shape in this embodiment, any other shape would be suitable as long as it can be handled relatively easily by a human operator.

As noted, dial indicator 15 is arranged to provide an indication of the volume of variable volume chamber 13. Thus, the dial indicator is provided with a first indicator pointer 20 which, during the occurrence of variations in the volume of variable volume chamber 13 would rotate at illustratively ten times the rate of rotation of a second indicator pointer 21.

FIG. 2 is a partially cross-sectional and fragmented side view of fluid contamination measurement arrangement 10. The cross-sectional views are taken along a cross-sectional plane defined by dashed line II—II shown in FIG. 1. FIG. 2 shows coupling portion 12 to have a substantially cylindrical internal wall 23 surrounding a microsyringe needle 24 which is adapted to fit on a nipple (not shown) attached to an hydraulic fluid system (not shown) which is to be monitored. The tip structure of microsyringe needle 24 is shown in the expanded representation, and is shown to have a beveled edge structure 25 and a longitudinal slit 26.

In this specific illustrative embodiment, coupling portion 12 is threaded into a screen holder 28 which contains therewithin a filter medium 30. Filter medium 30 is shown in this embodiment to be interposed between a pair of gasket seals 31 and 32, and there may be further provided an 0-ring seal 33 for ensuring that the fluid passing through the cannula of the microsyringe needle does not filter its way around the back side of filter medium 30.

Variable volume chamber 13 is shown to have a substantially cylindrical internal surface 35 which is in sealably sliding engagement with a piston assembly 37. In this specific illustrative embodiment, piston assembly 37 includes a double cup plunger 39 which is secured to a rod 40 by a screw 41.

Rod 40 is coupled in a known manner to an internal mechanism (not shown) of dial indicator 15, and may extend therethrough as rod 17 on the other side of the dial indicator. Dial indicator 15 is affixed to a bracket 43 which is provided with a cylindrical coupling portion 44 which is mechanically engaged with the variable volume chamber. Any known affixation method, such as screws 45, may be used to secure dial indicator 15 to bracket 43.

In operation, coupling portion 12 is engaged with a nipple (not shown) of the fluid system (not shown) to be monitored such that a pressurized fluid is conducted through microsyringe needle 24. The fluid passes through filter medium 30 and its own pressure may cause piston assembly 37 to move to the right. The displacement of piston assembly 37 is proportional to the volume of the fluid which has passed through filter medium 30. During such fluid flow, however, filter medium 30 which may be an electroformed screen, or some other filter medium as discussed hereinabove, accumulates particulate contaminants on the left side thereof until the filter medium is completely blocked. As noted, dial indicator 15, via pointers 20 and 21, provides an indication of the extent of displacement of the piston assembly. In one illustrative embodiment, first indicator pointer 20 may be arranged to complete ten revolutions for each inch of displacement of the piston assembly, and second indicator pointer 21 may be arranged to complete only one revolution for each such inch of displacement. It should be noted, however, that the use of dial indicator 15 is not essential to the practice of the invention since all that may be required to determine the amount of displacement of piston assembly 37 is a scale marked on rod 17. Alternatively, the rod need not be marked and the fluid contained within the variable volume chamber can be poured into a measurement cup. Such removal of the fluid contained within variable volume chamber 13 is achieved by applying a force at handle ball 18 so as to urge piston assembly 37 back to the position shown in FIG. 2. The fluid thus stored is forced through filter medium 30 in the reverse flow direction, thereby washing away the particulate contaminants which have accumulated on the left side thereof. Thus, by this simple operation, the piston assembly has been reset and the filter medium cleared for a subsequent measurement.

Figure 3:
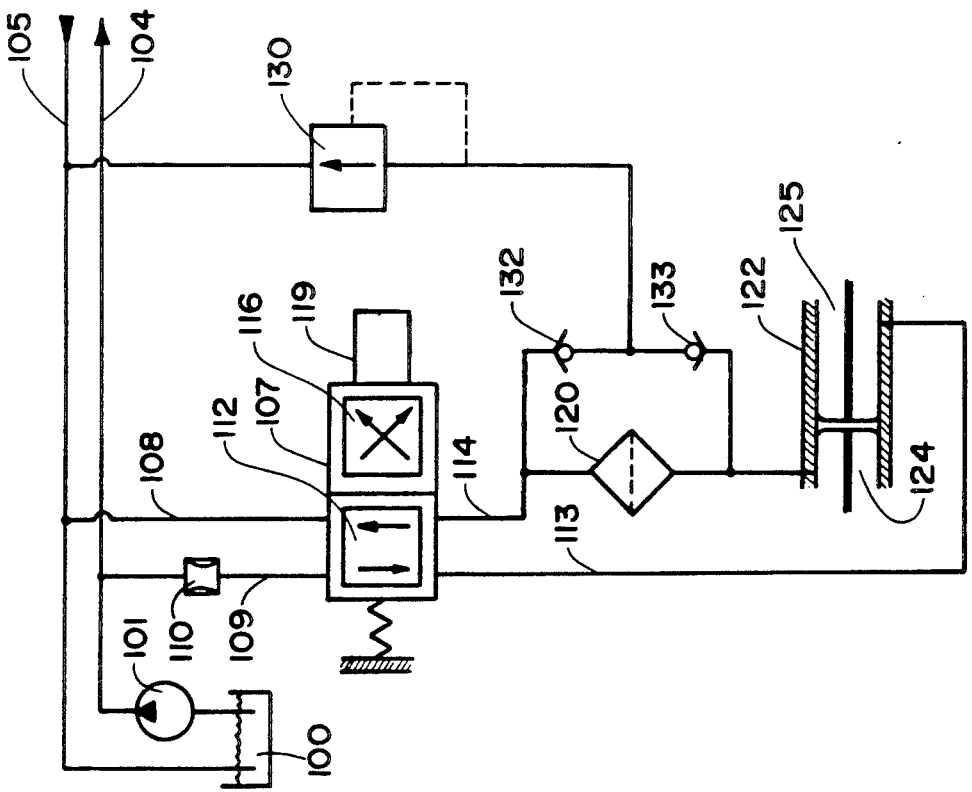
FIG. 3 is a schematic representation of a particulate contaminant measurement system in accordance with the invention.

FIG. 3 is a schematic representation of a contamination monitoring system suitable for continuous or automatically repeating monitoring of fluid contamination levels in a fluid system. As shown in this figure, a fluid system includes a fluid reservoir 100 and a pressurizing element 101 to produce high and low pressure lines 104 and 105, respectively. A bistable valve 107 is coupled to low pressure line 105 via a return line 108, and to high pressure line 104 via a supply line 109. In this embodiment, supply line 109 is provided with a restricting orifice 110 which reduces the flow rate through supply line 109 for purposes which will be described hereinbelow.

Bistable valve 107 has a first state 112 where the supply and return lines are coupled directly to a backflush line 113 and a filtration line 114. The bistable valve also has a second state 116 where supply line 109 is connected to filtration line 114, and return line 108 is connected to backflush line 113. Transference between the first and second states of the bistable valve is achieved by operation of a solenoid 119, in this specific illustrative embodiment.

The monitoring system further contains a filtration element 120 which is coupled to a variable volume chamber 122 having a filtration side 124 and a backflush side 125. The filtration element is coupled on both sides thereof to a relief valve 130 via upstream and return check valves 132 and 133, respectively. In some embodiments of the invention, relief valve 130 may be of the direct acting type which maintains a constant differential pressure across itself. This relief valve serves to limit the differential pressure which is developed across filtration element 120. The excess fluid which produces the excess pressure across the filtration element is returned to low pressure line 105.

At the start of the monitoring cycle in this specific embodiment, bistable valve 107 is placed in its second state by energization of solenoid 119. Thus, high pressure fluid is received from high pressure line 104, through restricting orifice 110, supply line 109, and filtration line 114 to filtration element 120. The fluid which passes through filtration element 120 is maintained in filtration side 124 of variable volume chamber 122; the displacement of the piston assembly within the variable chamber being indicative of the total fluid which has passed through filtration element 120. Any fluid which is present in backflush side 125 of the variable volume chamber is returned along backflush line 113 to return line 108. During this filtration portion of the monitoring cycle, upstream check valve 132 is opened, and return check valve 133 is closed, thereby providing a fluid path from filtration line 114 to relief valve 130 such that the pressure developed across the filtration element is limited thereby. This prevents damage to the filtration element.

As previously indicated, restricting orifice 110 is interposed between the high pressure line and the bistable valve to reduce the rate of flow. Thus, the pressure drop resulting from flow of the fluid through the upstream check valve and relief valve 130, and their associated fluid passageways, is small in comparison with the pressure setting of the relief valve.

Fluid continues to flow through filtration element 120 until it is completely blocked by accumulated particulate contaminants. In one practical embodiment of the invention, such complete blockage is produced within approximately 5 to 20 seconds after flow is initiated. After a time interval greater than the greatest expected time to block the filtration element, the displacement of the piston in the variable volume chamber is measured through any of several known techniques, including transducers, or reed switches located at suitable position intervals. This position, in certain embodiments of the invention, is recorded and held by the use of a sample and hold amplifier (not shown), or some other suitable device for recording or displaying the extent of displacement until the next monitoring cycle. Thus, the concentration of particulate contaminants is inferred from the displacement of the piston, whereby greater displacements correspond to lower concentrations.

The next phase of the monitoring cycle is the backflush phase. In this embodiment, solenoid 119 is de-energized thereby allowing bistable valve 107 to return to its first state 112. In this state, flow from the high pressure line is conducted through backflush line 113 to backflush side 125 of the variable volume chamber. Such an elevated pressure at the backflush side urges the piston assembly to the left, in this embodiment, thereby forcing the fluid stored in the filtration side back through filtration element 120 and through filtration and return lines 114 and 108, respectively. During this operation, return check valve 133 is opened and upstream check valve 132 is closed, thereby providing a fluid path to relief valve 130.

It may happen in certain applications that the filtration element becomes blocked from an accumulation of particulate contaminants in the backflush side thereof. In this event, the pressure in filtration side 124 will increase until relief valve 130 is opened, thereby allowing the piston to complete its stroke to the left. In this manner, the piston is permitted to attain its zero position for the next monitoring cycle, notwithstanding the reverse blockage of the filtration element.

In an automatic embodiment of the invention, an automatic timer (not shown) controls the tire until the beginning of the next monitoring cycle. However, the minimum time allowed for the backflush phase should be the actual time required to complete backflushing. The completion of backflushing can be determined by sensing that the piston assembly within the variable volume chamber is in its leftmost position. It should be noted that in a practicable embodiment of the invention, the life of the filtration element is extended by increasing the cycle times. Additionally, the volume of fluid which is required to flow between the high pressure line and the filtration element should be minimized to maximize the accuracy of the system. Thus, in certain embodiments, the filtration element may be integrated into a monitoring unit (not shown) which further includes the bistable valve, the solenoid, the variable volume chamber with its piston assembly therein, the relief valve, and the check valves. Alternatively, the upstream check valve and the return check valve can be combined into a single unit which is commercially available and known as a double check, or shuttle, valve.

Figure 4:
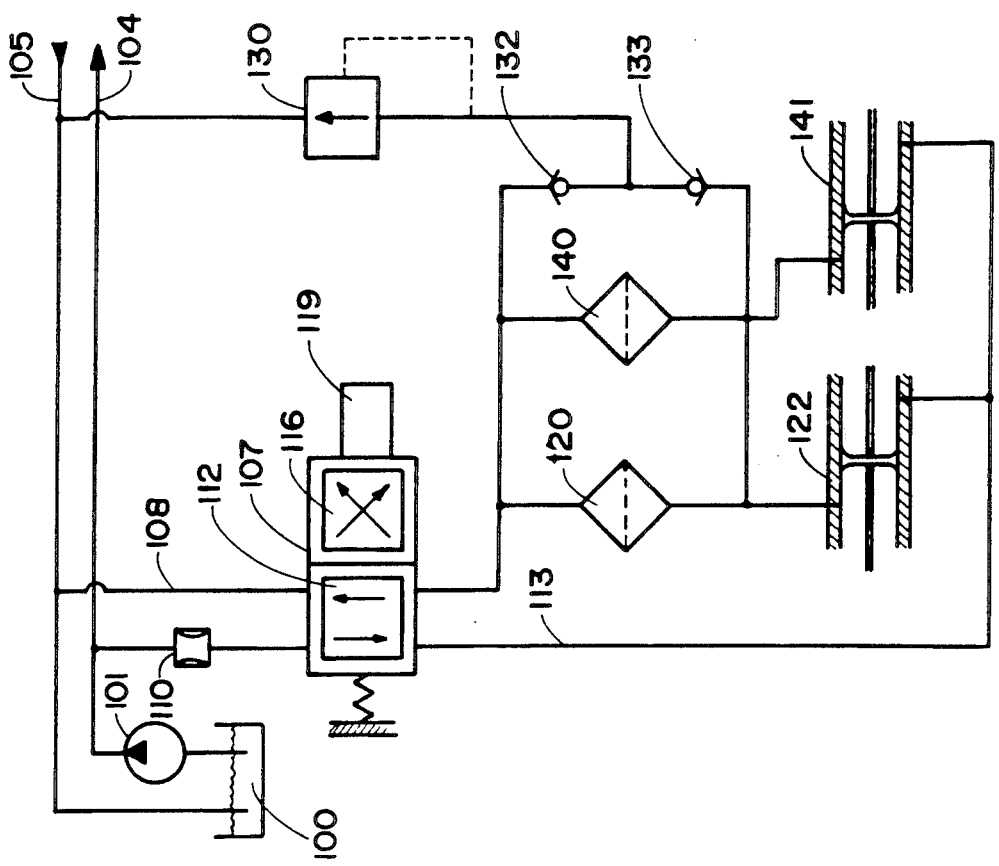
FIG. 4 is a schematic representation of a particulate contaminant monitoring system utilizing a plurality of filter media and associated fluid volume measurement arrangements.

FIG. 4 is a schematic representation of an embodiment of the invention which is similar to that described hereinabove with respect to FIG. 3, but is provided with an additional filtration element 140 and additional variable volume chamber 141 for providing contamination measurements in several size ranges. More specifically, filtration elements 120 and 140 contain within them filter media having filtration pores of different dimensions. This provides the advantage that the level of a specific type of contamination, to the extent that it can be characterized by particle size, can be monitored. In every other respect, this dual range monitoring arrangement operates in the manner described hereinabove with respect to FIG. 3. Elements of structure in the embodiment of FIG. 4 which have analogous correspondence to elements of structure in the embodiment of FIG. 3 are similarly designated.

Figure 5:
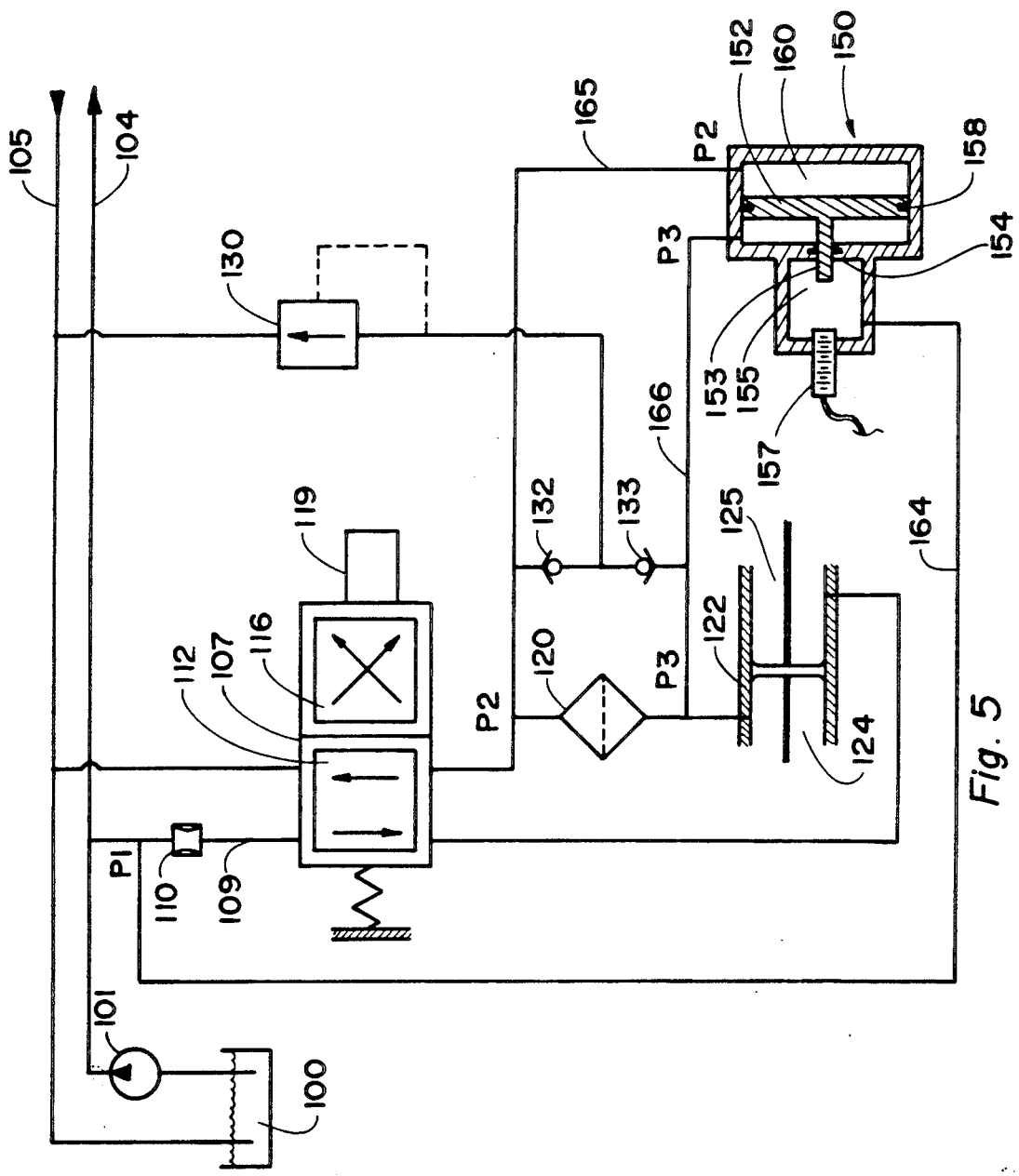
FIG. 5 is a schematic representation of an embodiment of a particulate contaminant monitoring system utilizing differential pressures to determine reduction of a flow rate through a filter medium.

FIG. 5 is a schematic representation of a particulate contaminant monitoring arrangement which does not require that the filter medium become completely blocked during each monitoring cycle. In essence, the embodiment of FIG. 5 produces a signal at the end of the filtering phase which indicates that the differential pressure developed across the filtration element is a predetermined proportion $1/K \times 100\%$ of the pressure differential across the restricting orifice. In this figure, elements of structure having analogous correspondence to elements noted hereinabove with respect to the embodiment of FIG. 3 are similarly designated.

The embodiment of FIG. 5 is provided with a pressure differential monitoring device 150 which contains a plunger arrangement 152 slidably enclosed therein. Plunger 152 has a rod portion 153 which extends through an internal wall 154 to a chamber 155. Chamber 155 is provided with a sensor 157 which may be a limit switch, a proximity switch, or some other commercially available device which signals when plunger 152 and rod 153 are in their leftmost position.

Plunger 152 is provided with a circumferential seal 158 so as to produce two chambers 160 and 161 on either side thereof. The bore surrounding the rod is similarly sealed.

Each of chambers 155, 160, and 161 are pressurized by respective ones of pressure signal lines 164, 165, and 166. Pressure signal line 164 couples chamber 155 to a point between restricting orifice 110 and high pressure line 104. This pressure is indicated as $P_1$. Chamber 160 receives a pressure $P_2$ via pressure signal line 165 which corresponds to the pressure between filtration element 120 and bistable valve 107. Finally, chamber 161 receives a pressure $P_3$ via a pressure signal line 166 which corresponds to the pressure between filtration element 120 and filtration side 124 of variable volume chamber 122. Thus, when bistable valve 107 is in its second state 116, the pressure across restriction orifice 110 is $P_1 - P_2$. The pressure across filtration element 120 is $P_2 - P_3$.

In operation, it is assumed that an indication is desired when $(P_2 - P_3)$ equals $(P_1 - P_2)/K$. Thus, the filtration phase should be completed when the pressure across the filtration elements reaches a predetermined percentage $1/K \times 100\%$ pressure across the restricting orifice. This is achieved in pressure differential monitoring device 150 by configuring the mechanism such that the surface areas presented to the various pressure signals have a preselected proportion ratio with respect to each other. More specifically, the cross-sectional surface area of rod 153 is $A_R$, the surface area of the plunger which faces chamber 161 is $KA_R$, and the back surface area of the plunger which faces chamber 160 is $(K+1)A_R$. In other words, the cross-sectional surface area of chambers 160 and 161, which is referred to herein as $A_B$, has a fixed relationship with respect to the cross-sectional area of rod 153 in that $A_B = (K+1)A_R$. Thus, the surface areas of rod 153 and plunger 152 which face chambers 155, 161, and 160, respectively, correspond to the ratio $1:K:(K+1)$.

In operation, as long as $(P_2 - P_3)$ is less than $1/K \times 100\%$ of $(P_1 - P_2)$, the hydraulic force to the right, which is $P_1 A_R + P_3(A_B - A_R)$, is greater than $P_2 A_B$, which is the hydraulic force to the left. Thus, the plunger will remain in its rightmost position. However, when the pressure across the filtration element increases such that $(P_2 - P_3)$ is greater than $1/K \times 100\%$ of $(P_1 - P_2)$, the plunger will shift to the left. Such leftward displacement is detected by sensor 157, and serves to terminate the filtration phase of the monitoring procedure.

It is an advantage of the present embodiment that the comparison of pressures essentially removes the effects of viscosity in the measurement. Additionally, the rate of fluid flow will not affect the measurement of the degree of flow restriction.

In this embodiment, as well as the other embodiments described herein, the method of operation includes the steps of passing a portion of the fluid through the filter medium in a first flow direction, and measuring the volume of such fluid until the rate of flow of the fluid is reduced to a predetermined rate of flow, as a result of blockage of the filter medium. Of course, the reduced rate of flow may be zero flow or some value greater than zero. Subsequently, the filter medium is cleared by backflushing the fluids therethrough. In some embodiments of the invention, such backflushing is achieved by reversing the high and low pressure portions of the fluid system with respect to the filter medium.

Figure 6:
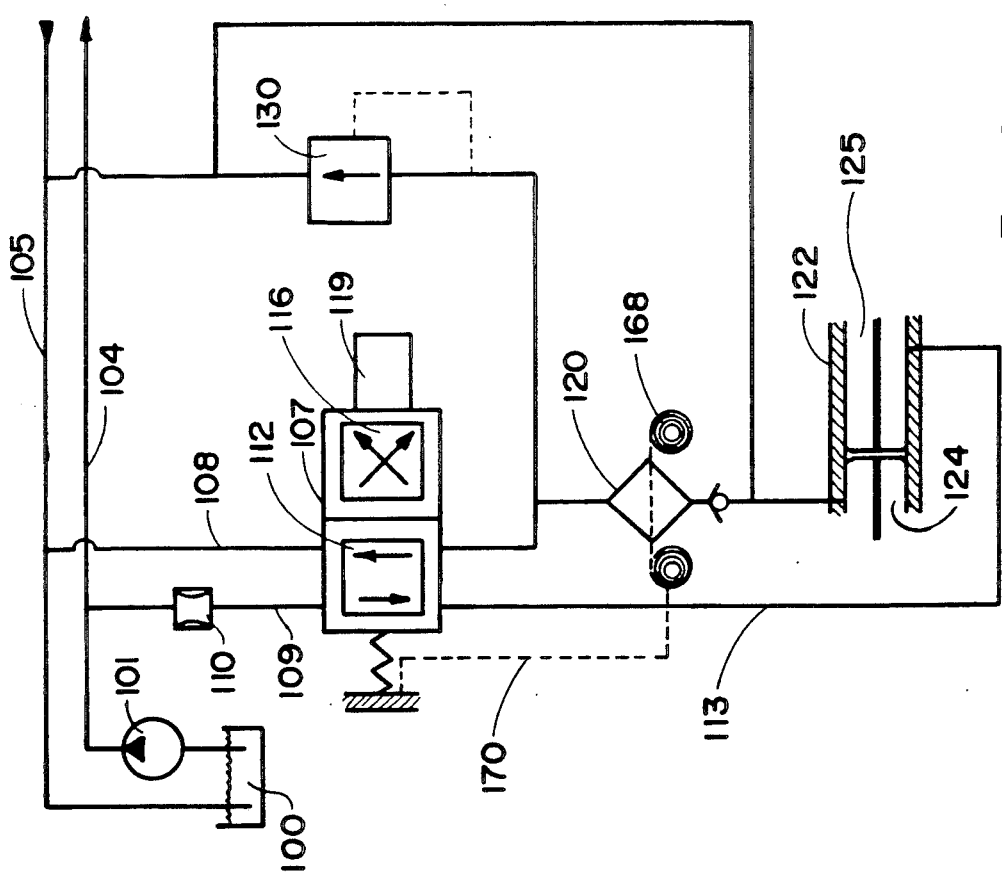
FIG. 6 is a schematic representation of a particulate contaminant monitoring system utilizing an in-line contaminant sampling unit.

FIG. 6 is a schematic representation of an in-line contaminant sampling unit, incorporated into the continuous or automatically repeating monitoring system previously illustrated in FIG. 3. As shown in FIG. 6, the filtration element 120 is further provided with an advancement and take up reel system 168 that advances a continuous filter media on a frame by frame basis. The movement of the frames of the filter are operatively coordinated with the action of the bistable valve 107 as indicated by the dashed line 170. As such, the in-line contaminant sampling unit measures the contaminant levels on a time interval basis (say, once an hour). The chronological sequence of frames are numbered and/or recorded and represent a contaminant history of the system. The collected samples of contaminant on the respective frames can be analyzed later (microscopically, spectroscopically, and the like) for the presence and quantity of wear-debris. This data can then be interpreted as a measure of the overall status of the hydraulic system being monitored. It should be appreciated that such an in-line contaminant sampling unit and feature can also be employed in a nonbackflush mode or unit as well as the embodiments illustrated in FIGS. 3 and 6.

Although the invention has been described in terms of specific embodiments and applications, persons skilled in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A contamination measurement arrangement for determining a level of particulate contamination of a fluid, the contamination measurement arrangement comprising:

porous filtration means having filtration pores therethrough for passing the fluid, said filtration pores each having respective effective filtration dimensions within a predetermined range of filtration dimensions whereby oversided particles of the particulate contamination in the fluid having respective particle dimensions greater than said predetermined range of filtration dimensions are prevented from passing through said filtration pores;

volume indicator means for producing an indication responsive to a volume of the fluid which has passed through said filtration pores of said porous filtration means in a first direction of fluid flow; and backflush means for urging the fluid through said filtration pores in a second direction of fluid flow whereby ones of said oversized particles of the particulate contamination which have accumulated at said porous filtration means as flushed away therefrom, said backflush means comprises:

filtrate chamber means for receiving said volume of the fluid which has passed through said filtration pores of said porous filtration means, and piston means slidably arranged within said filtrate chamber means for defining a volume of said filtrate chamber means responsive to said volume of the fluid which has passed through said filtration pores of said porous filtration means, and means indicating a location of said piston means within said filtrate chamber means.

2. The contamination measurement arrangement of claim 1 wherein said backflush means further comprises actuator means coupled to said piston means for applying a backflush force and urging said piston means slidably in a backflush direction which reduces said volume of said filtrate chamber means.

3. The contamination measurement arrangement of claim 2 wherein said actuator means comprises rod means coupled to said piston means for transmitting said backflush force to said piston means.

4. The contamination arrangement of claim 2 wherein said actuator means comprises hydraulic actuator means responsive to a fluid pressure for urging said piston means in said backflush direction.

5. The contamination measurement arrangement of claim 4 wherein the fluid is installed in a fluid system having a high pressure portion and a low pressure portion, said hydraulic actuator means being responsive to a fluid pressure from the high pressure portion of the fluid system.

6. The contamination measurement arrangement of claim 5 wherein the fluid is urged to pass through the filtration pores in response to a fluid pressure from the high pressure portion of the fluid system.

7. The contamination measurement arrangement of claim 6 wherein there is further provided selectable fluid coupling means for coupling the high pressure portion of the fluid system to a selectable one of said porous filtration means and said hydraulic actuator means.

8. The contamination measurement arrangement of claim 7 wherein there is further provided safety relief means for limiting a fluid pressure applied to said porous filtration means.

9. A contamination monitoring system for monitoring automatically a level of particulate contamination of a fluid in a fluid system having a first portion having an elevated fluid pressure and a second portion having lower fluid pressure than said first portion, said contamination monitoring system comprising:

porous filtration means having filtration pores therethrough for passing the fluid, said filtration pores each having respective filtration dimensions whereby oversized particles of the particulate contamination in the fluid having respective particle dimensions greater than said first predetermined range of filtration dimensions are prevented from passing through said filtration pores, said porous filtration means being coupled to the fluid system whereby fluid flows from the first portion thereof, through said porous filtration means, and to the second portion the fluid system;

flow reversal means having first and second flow states and coupled to the first portion of the fluid system and to said porous filtration means whereby when said flow reversal means is in said first flow state, the fluid flows through said porous filtration means in a first flow direction, and when said flow reversal means is in said second flow state, the fluid flow through said porous filtration means in a second flow direction; and filtrate chamber means for storing and thereby indicating the volume of the fluid which has passed through said porous filtration means in said first flow direction and backflush chamber means for receiving the fluid when said flow reversal means is in said second flow state whereby at least a portion of said volume stored in said filtrate chamber means is urged through said porous flow means in said second flow direction.

10. The contamination monitoring system of claim 9, wherein there is further provided pressure relief means coupled to said porous filtration means for limiting a fluid pressure differential thereacross.

11. The contamination monitoring system of claim 10 wherein there are further provided first and second check valve means for coupling said porous filtration means to said pressure relief means.

12. The contamination monitoring system of claim 10 wherein said pressure relief means comprises a direct acting relief valve for maintaining a substantially constant differential pressure across itself.

13. The contamination monitoring system of claim 9, wherein there is further provided flow restriction means for reducing a flow rate of the fluid from the first portion of the fluid system through said porous filtration means.

14. A contamination monitoring system for monitoring automatically a level of particulate contamination of a fluid in a fluid system having a first portion having an elevated fluid pressure and a second portion having lower fluid pressure than said first portion, said contamination monitoring system comprising:

porous filtration means having filtration pores therethrough for passing the fluid, said filtration pores each having respective filtration dimensions within a first predetermined range of filtration dimensions whereby oversized particles of the particulate contamination in the fluid having respective particle dimensions greater than said first predetermined range of filtration dimensions are prevented from passing through said filtration pores, said porous filtration means being coupled to the fluid system whereby fluid flows from the first portion thereof, through said porous filtration means, and to the second portion of the fluid system;

flow reversal means having first and second flow states and coupled to the first portion of the fluid system and to said porous filtration means whereby when said flow reversal means is in said first flow state, the fluid flows through said porous filtration means in a first flow direction, and when said flow reversal means is in said second flow state, the fluid flows through said porous filtration means in a second flow direction;

flow restriction means for reducing a flow rate of the fluid from the first portion of the fluid system through said porous filtration means; and pressure comparator means for comparing a filtration pressure across said porous filtration means against a flow restriction pressure across said flow restriction means.

15. The contamination monitoring system of claim 14 wherein said pressure comparator means comprises pressure differential indicator means for producing an indication responsive to said filtration pressure exceeding a predetermined portion ($1/K \times 100\%$), where K is greater than one of said flow restriction pressure.

16. The contamination monitoring system of claim 15 wherein said pressure differential indicator means comprises:

stator means having first and second chambers for receiving pressure signals corresponding to said filtration and flow restriction pressures; and rotor means slidably engaged in said stator means for presenting a plurality of surfaces to respective ones of said pressure signals, said surfaces having a predetermined proportion ratio of surface areas with respect to each other.

17. The contamination monitoring system of claim 16 wherein said rotor means presents first, second, and third surfaces to respective ones of first, second, and third pressure signals, said surfaces having respective surface areas being proportionally related to one another by a ratio $1:K:(K+1)$, respectively, whereby said rotor means is displaced when said filtration pressure exceeds $1/K \times 100\%$ of said flow restriction pressure, where K is greater than one.

18. contamination monitoring system of claim 17 wherein there is further provided sensor means for producing an indication responsive to said displacement of said rotor means.

19. The contamination monitoring system of claim 17 wherein said first and second pressure signals correspond to a pressure differential across said flow restriction means, and said second and third pressure signals correspond to a pressure differential across said porous filtration means.

20. A contamination monitoring system for monitoring automatically a level of particulate contamination of a fluid in a fluid system having a first portion having an elevated fluid pressure and a second portion having lower fluid pressure than said first portion, said contamination monitoring system comprising:

porous filtration means having filtration pores therethrough for passing the fluid, said filtration pores each having respective filtration dimensions whereby oversized particles of the particulate contamination in the fluid having respective particle dimensions greater than a first predetermined range of filtration dimensions are prevented from passing through said filtration pores, said porous filtration means being coupled to the fluid system whereby fluid flows from the first portion thereof, through said porous filtration means, and to the second portion of the fluid system;

flow reversal means having first and second flow states and coupled to the first portion of the fluid system and to said porous filtration means whereby when said flow reversal means is in said first flow state, the fluid flows through said porous filtration means in a first flow direction, and when said flow reversal means is in said second flow state, the fluid flows through said porous filtration means in a second flow direction;

volume indicator means for providing an indication responsive to a volume of the fluid which has passed through said porous filtration means in said first flow direction;

a further porous filtration means having filtration pores therethrough for passing the fluid, said filtration pores each having respective effective filtration dimensions within a second predetermined range of filtration dimensions whereby oversized particles of the particulate contamination in the fluid having respective particle dimensions greater than said second range of filtration dimensions are prevented from passing through said filtration pores, said further porous filtration means being coupled to the fluid system whereby fluid flows from the first portion thereof, through said further porous filtration means, and to the second portion of the fluid system; and second volume indicator means for providing an indication responsive to a volume of the fluid which has passed through said further porous filtration means in said first direction of fluid flow.

21. A method of determining the level of particulate contaminants in a fluid of a fluid system, the method comprising the steps of:

passing a portion of the fluid in a first flow direction through a filter medium having pores therethrough of a predetermined maximum size and through a restriction orifice which is interposed between said filter medium and the fluid system;

monitoring pressure differentials across said filter medium and said restriction orifice, respectively; and producing an indication when said pressure differential across said filter medium exceeds a predetermined proportion (K%) of said pressure differential across said restriction orifice;

measuring a volume of the fluid which has passed through the filter medium until a rate of flow of the fluid therethrough is reduced to a predetermined rate of flow as a result of blockage of the filter medium by particulate contaminants having particles sizes greater than said predetermined maximum size;

backflushing by passing said portion of the fluid through said filter medium in a second flow direction whereby said particulate contaminants blocking said filter medium are flushed away therefrom.

22. A contamination monitoring system for monitoring automatically a level o particulate contamination of a fluid in a fluid system having a first portion having an elevated fluid pressure and a second portion having lower fluid pressure than said first portion, said contamination monitoring system comprising:

porous filtration means having filtration pores therethrough for passing the fluid, said filtration pores each having respective filtration dimensions whereby oversized particles of the particulate contamination in the fluid having respective particle dimensions greater than said first predetermined range of filtration dimensions are prevented from passing through said filtration pores, said porous filtration means being coupled to the fluid system whereby fluid flows from the first portion thereof, through said porous filtration means, and to the second portion of the fluid system;

flow reversal means having first and second flow states and coupled to the first portion of the fluid system and to said porous filtration means whereby when said flow reversal means is in said first flow states, the fluid flows through said porous filtration means in a first flow direction, and when said flow reversal means is in said second flow state, the fluid flows through said porous filtration means in a second flow direction;

volume indicator means for providing an indication responsive to a volume of the fluid which has passed through said porous filtration means in said first flow direction;

pressure relief means coupled to said porous filtration means for limiting a fluid pressure differential thereacross; and first and second check valve means for coupling said porous filtration means to said pressure relief means.

23. A contamination measurement arrangement for determining a level of particulate contamination of a fluid, the contamination measurement arrangement comprising:

a plurality of at least two porous filtration means each having filtration pores therethrough for simultaneously passing the fluid, said filtration pores each having respective effective filtration dimensions within a predetermined range of filtration dimensions whereby oversized particles of the particulate contamination in the fluid having respective particle dimensions greater than said predetermined range of filtration dimensions are prevented from passing through said filtration pores, the predetermined range of each filtration means being different than that of the other filtration means;

plural volume indicator means, one for reach of said filtration means, for separately and simultaneously producing a different indication responsive to the volume of the fluid which has passed through said filtration pores of each of said porous filtration means in a first direction of fluid flow; and backflush means for urging the fluid through said filtration pores of each of said filtration means in a second direction of fluid flow whereby one of said oversized particles of the particulate contamination which have accumulated at each of said porous filtration means are flushed away therefrom.

* * * * *